(12) United States Patent
Chen (10) Patent No.: US 6,411,860 B1
(45) Date of Patent: *Jun. 25, 2002

(54) METHOD FOR EXTRACTING AND CLASSIFYING SHEET VARIATION PATTERNS FROM TWO-DIMENSIONAL SHEET MEASUREMENTS

(75) Inventor: Shih-Chin Chen, Dublin, OH (US)

(73) Assignee: ABB Industrial Systems, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/243,165

(22) Filed: Feb. 2, 1999

Related U.S. Application Data
(60) Provisional application No. 60/074,232, filed on Feb. 10, 1998.

(51) Int. Cl.[7] .................................................. G06F 7/66
(52) U.S. Cl. .......................... 700/129; 700/28; 162/263
(58) Field of Search ............................ 700/129, 38, 53, 700/117, 122; 702/81, 84, 189; 162/263, 271

(56) References Cited

U.S. PATENT DOCUMENTS

| | | | | |
|---|---|---|---|---|
| 5,301,129 A | * | 4/1994 | McKaughan et al. | 382/149 |
| 5,393,378 A | | 2/1995 | Yakabe et al. | 162/61 |
| 5,400,247 A | * | 3/1995 | He | 700/53 |
| 5,400,258 A | * | 3/1995 | He | 700/129 |
| 5,539,634 A | * | 7/1996 | He | 700/38 |
| 5,563,809 A | * | 10/1996 | Williams et al. | 702/84 |
| 5,684,707 A | * | 11/1997 | Rogowski | 700/129 |
| 5,893,055 A | * | 4/1999 | Chen | 702/189 |
| 5,960,374 A | * | 9/1999 | Lausier | 702/81 |
| 6,026,334 A | * | 2/2000 | Kayihan et al. | 700/28 |
| 6,094,604 A | * | 6/2000 | Bucher et al. | 700/129 |
| 6,086,237 A | * | 7/2000 | Gorinevsky et al. | 700/127 |
| 6,233,495 B1 | * | 5/2001 | Chen | 700/122 |

* cited by examiner

*Primary Examiner*—Thomas Black
*Assistant Examiner*—Ronald D Hartman, Jr.
(74) *Attorney, Agent, or Firm*—Stevens & Showalter, LLP (57) ABSTRACT

Multiple two-dimensional variation patterns are extracted from two-dimensional sheet measurement data of sheet material being manufactured with the variation patterns being classified to identify the causes of the extracted patterns. The extracted two-dimensional variation patterns are identified with the elements or components of the process or machine which caused the patterns. The machine components which cause the variation patterns can then be adjusted and/or controlled so that the patterns can be reduced or substantially eliminated in sheets of material produced by the machine. In addition to adjustment and/or control of the process or machine producing the sheet of material, the extracted variation patterns can be used as new representations of sheet quality, process or machine quality and the patterns will provide more in-depth understanding for operators of the machine.

21 Claims, 9 Drawing Sheets

METHOD FOR EXTRACTING AND CLASSIFYING SHEET VARIATION PATTERNS FROM TWO-DIMENSIONAL SHEET MEASUREMENTS

CROSS-REFERENCE TO RELATED APPLICATIONS

This application claims the benefit of U.S. Provisional Application No. 60/074,232, filed Feb. 10, 1998, which is incorporated herein by reference.

BACKGROUND OF THE INVENTION

Traditionally, scanning sensors are applied in sheet forming processes to measure sheet property variability. Unfortunately, while the sensors scan across a forming sheet in the cross-machine direction (CD), the sheet is very rapidly moving past the scanning sensors in the machine direction (MD). The scanning sensors, thus, actually measure only a zigzag path on the two-dimensional sheet being formed. Using this scanning technique, there is no easy way to completely separate the real sheet variations occurring in the machine direction from the real sheet variations occurring in the cross-machine direction. In addition, since the sensors measure only along a zigzag path scanned on a two-dimensional sheet, the majority of the sheet is not measured at all. With these inherent limitations of a scanning mechanism, the measurements obtained from a scanning sensor are very sparse and can only be used to roughly approximate the real sheet MD, CD, and residual variations. Any further analysis of sheet variations based on a scanning measurement is severely limited by the fact that the raw measurement itself is not an easily separable two-dimensional measurement.

Recently, non-scanning, full-sheet measurement has become commercially available to measure the entire sheet width without movement of sensors back and forth across the sheet and without missing any portions of the sheet, see U.S. Pat. No. 5,563,809 which is incorporated herein by reference. Such measurements can be taken at many locations along a sheet-forming process. Using these measuring techniques, a massive amount of full-width, truly two-dimensional (2D) measurement data is available almost continuously. These measurements contain profound information about sheet variations which have not been observed with conventional scanning techniques used before.

To fully utilize all information contained in these two-dimensional measurements, the two-dimensional measurement data cannot be processed as in the past. Accordingly, there is a need for improved and novel processing techniques which can extract and classify useful information about sheet variations so that persons using the measurement equipment can readily recognize different types of variations and identify the causes of the variations in the process which is manufacturing the sheet being measured.

SUMMARY OF THE INVENTION

This need is met by the invention of the present application wherein multiple two-dimensional variation patterns are extracted from two-dimensional sheet measurement data of a sheet of material taken as the sheet is being manufactured and classified to identify the causes of the extracted patterns. The extracted two-dimensional variation patterns are identified with the elements in the process which caused the patterns, i.e., components of the machine making the sheet. The elements of the process which cause the patterns can then be adjusted and/or controlled so that the patterns can be reduced or substantially eliminated in sheets of material produced by the process. In addition to adjustment and/or control of the process or machine producing the sheet of material, the extracted variation patterns can be used as new representations of sheet quality, process or machine quality and the patterns will provide more in-depth understanding for operators of the machine.

DETAILED DESCRIPTION OF THE INVENTION

The extraction and classification of multiple two-dimensional (2D) variation patterns from two-dimensional measurement data is performed using analysis methods derived from advanced image processing techniques and mathematical concepts in function space analysis. A raw two-dimensional sheet variation measurement appears as a two-dimensional array continuously growing in the machine direction as the sheet is produced. By selecting a proper interval in the machine direction (MD) and the cross-machine direction (CD), the two-dimensional measurement of sheet variations, or sheet quality variations, can be viewed as a two-dimensional image or a function of two independent variables as described in U.S. patent application Ser. No. 08/865,717, filed May 30, 1997 and entitled TWO-DIMENSIONAL WEB PROPERTY VARIATION MODELING AND CONTROL, now U.S. Pat. No. 5,893,055, which is incorporated by reference herein. In the discretized form, the sheet variations can be represented as a matrix (or a two-dimensional array) as:

$$Y=[y(i,j)]_{n \times m} \quad (1)$$

where
- i is the index of discrete points in the cross-machine direction,
- j is the index of discrete points in the machine direction,
- n is the number of discrete points in the cross-machine direction, and
- m is the number of discrete points in the machine direction.

The idea of two-dimensional (2D) pattern analysis of sheet variability is to decompose Y into several classes of variation patterns. As one example, Y can be decomposed into MD variations, CD variations, diagnosis variations, and unclassifiable random variations. That is:

$$Y=Y_{md}+Y_{cd}+Y_d+Y_u \quad (2)$$

where
- $Y_{md}$ represents the class of MD variations,
- $Y_{cd}$ represents the class of CD variations,
- $Y_d$ represents the class of diagnosis variations, and
- $Y_u$ represents the unclassifiable random variations.

Within each class, the variations can be further decomposed into even more detailed patterns in order to identify or associate those patterns with their corresponding actuators or the root causes of the variations. For example, the MD variations and CD variations can be further separated into controllable and uncontrollable as:

$$Y_{md}=Y_{cm}+Y_{um} \quad (3)$$

$$Y_{cd}=Y_{cc}+Y_{uc} \quad (4)$$

where
- $Y_{cm}$ are variations controllable with MD actuators,
- $Y_{um}$ are variations uncontrollable with MD actuators,
- $Y_{cc}$ are variations controllable with CD actuators, and
- $Y_{uc}$ are variations uncontrollable with CD actuators.

Similarly, the diagnosis variation $Y_d$ can be separated as:

$$Y_d=Y_{d1}+Y_{d2}+Y_{d3}+\ldots \quad (5)$$

where
- $Y_{d1}$ is a first diagnostic variation pattern,
- $Y_{d2}$ is a second diagnostic variation pattern,
- $Y_{d3}$ is a third diagnostic variation pattern, and so on.

Depending on the applications, the uncontrollable portions of the MD variations and the CD variations can also be considered as parts of diagnosis variations. In other words, the sheet variations Y can also be decomposed into controllable MD variations $Y_{cm}$, controllable CD variations $Y_{cc}$, diagnosis variations $Y_d$, and unclassifiable variations $Y_u$ as shown in equation (6):

$$Y=Y_{cm}+Y_{cc}+Y_d+Y_u \quad (6)$$

Based on the needs of applications and the practical considerations of implementation, the following classifications may also be appropriate:

$$Y=Y_{cm}+Y_{cd}+Y_d+Y_u \quad (7)$$

$$Y=Y_{md}+Y_{cc}+Y_d+Y_u \quad (8)$$

The main difference among equations (2), (6), (7), and (8) is whether the uncontrollable MD and/or uncontrollable CD variations are part of $Y_d$ or not. For illustration purposes, the classifications of equation (8) will be used to describe the technique of pattern separations for the remainder of the description.

The technique of extracting variation patterns from a sheet variation measurement or image can be illustrated with an example of a 2D measurement image obtained from a paper making machine which produces fine writing and printing paper. In this example, the 2D sheet variation is measured with a non-scanning full sheet optical sensing system. The array of data represents the measurement of a sheet with CD width of 200 cm and MD interval of 60 minutes. If machine speed is considered, the MD time interval can be converted into a length. However, in the following description, we will use time as the index of the MD variable.

Figure 1:
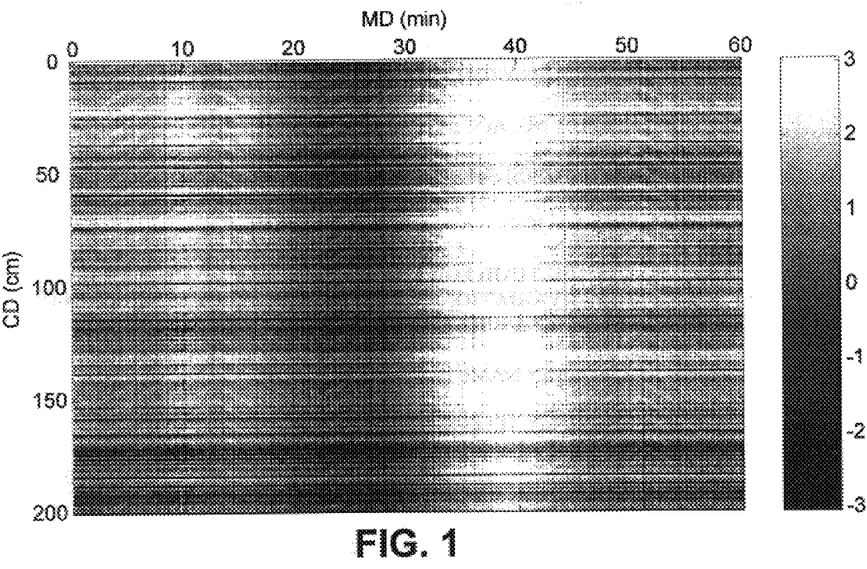
FIG. 1 is an image of raw measurement data of 2D sheet variations.
Figure 2:
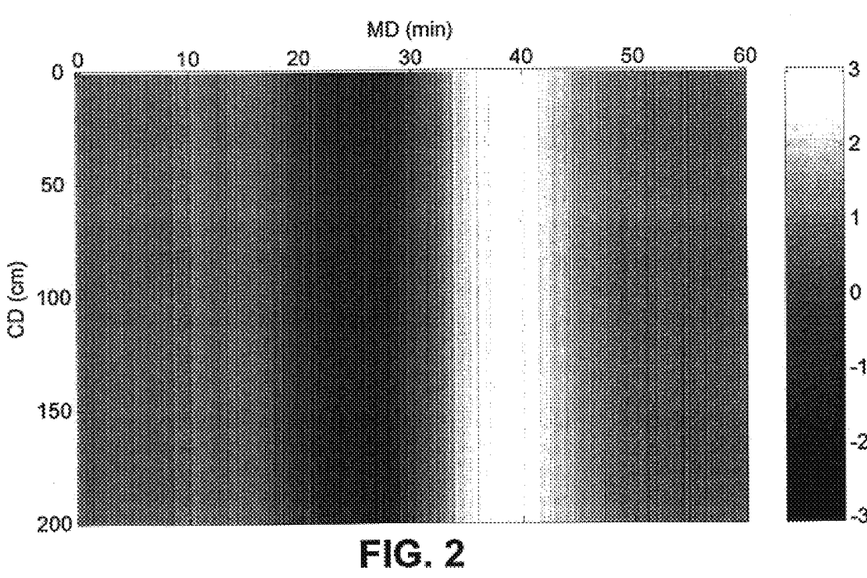
FIG. 2 is an image of pure MD variations or variation patterns extracted from the 2D sheet variations of FIG. 1.
Figure 3:
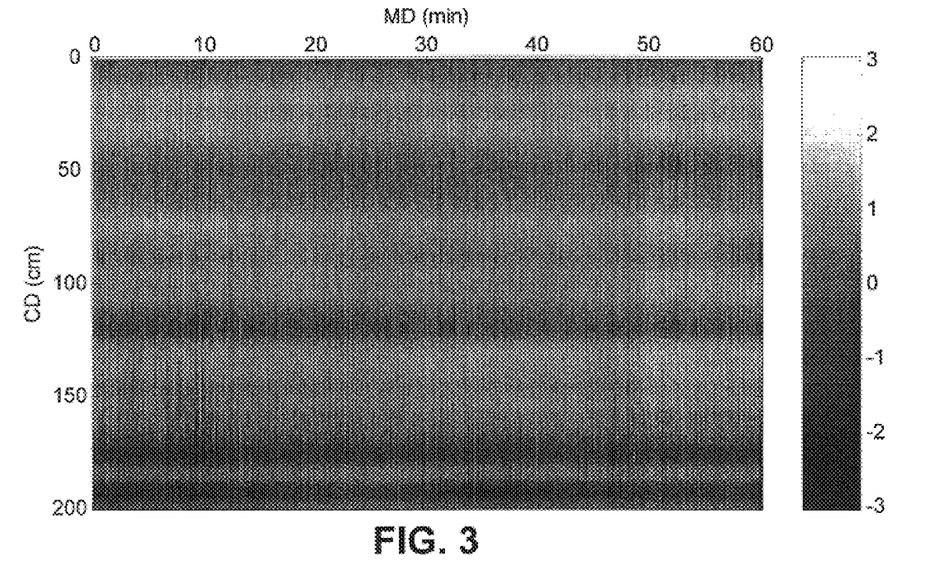
FIG. 3 is an image of controllable CD variations or variation patterns extracted from the 2D sheet variations of FIG. 1.
Figure 4:
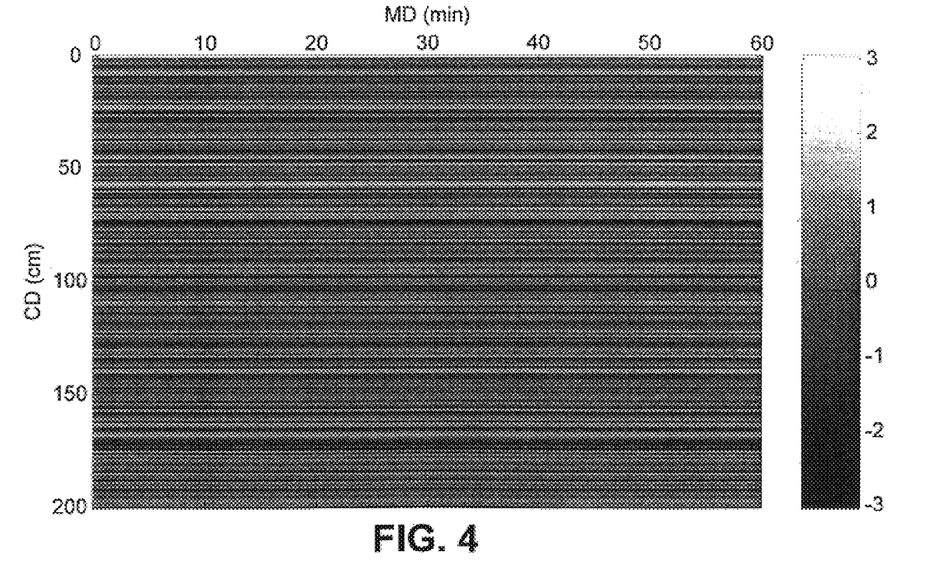
FIG. 4 is an image of uncontrollable CD variations or variation patterns extracted from the 2D sheet variations of FIG. 1.
Figure 5:
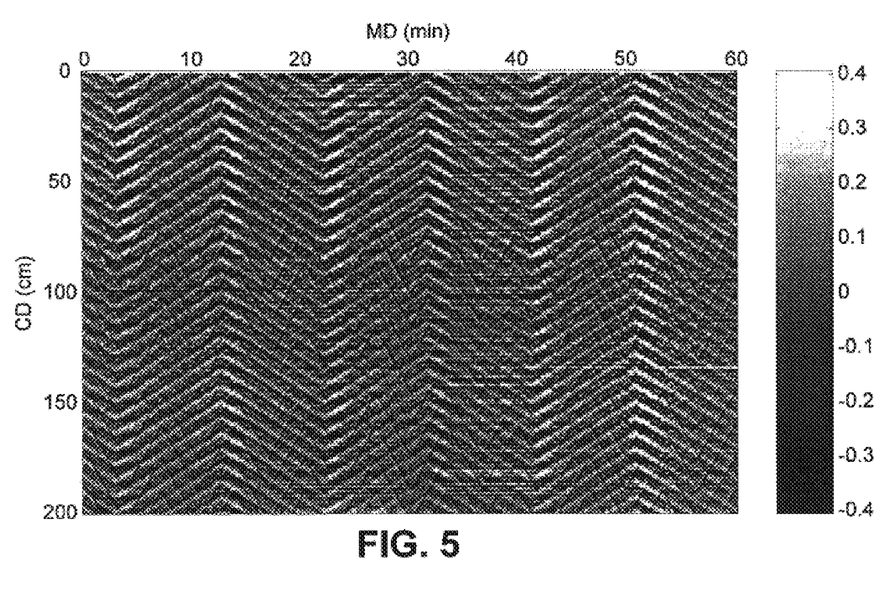
FIG. 5 is an image of diagnostic variations or variation patterns extracted from the 2D sheet variations of FIG. 1.
Figure 6:
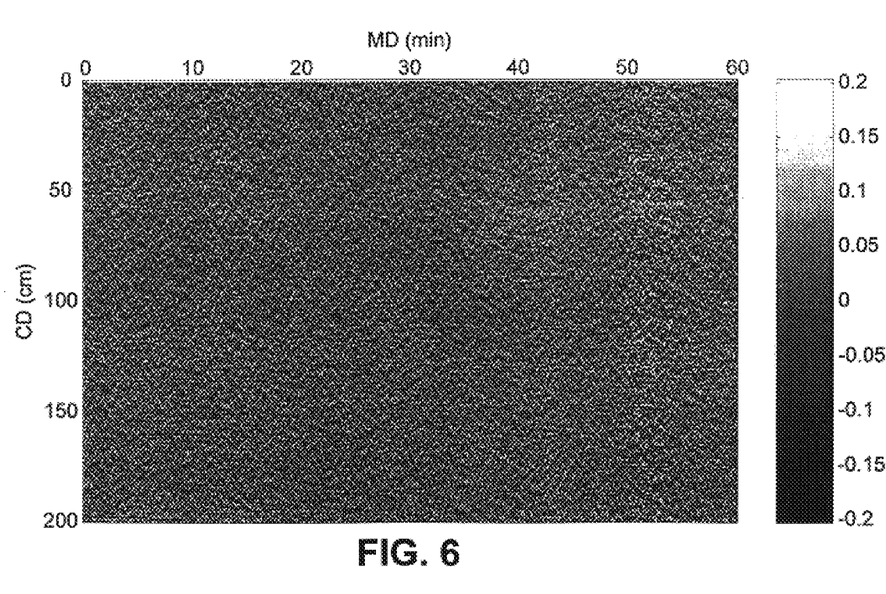
FIG. 6 is an image of the remaining unclassifiable random variations after the pure MD and CD variations and diagnostic variations have been extracted from the 2D sheet variations of FIG. 1.

FIG. 1 shows an image view of a raw measurement Y of 2D sheet variations without any decomposition, i.e., an image of raw measurement data. The pure MD variations $Y_{md}$ are extracted from Y and displayed in FIG. 2. The controllable CD variations $Y_{cc}$ are shown in FIG. 3 and uncontrollable CD variations $Y_{uc}$ are shown in FIG. 4. FIG. 5 displays the diagnosis variations $Y_d$. FIG. 6 shows the remaining unclassifiable random variations $Y_u$. The diagnostic variations or diagnostic variation pattern $Y_d$ of FIG. 5 can also be further separated into the detailed diagnostic variation patterns 1 and 2, or sub-patterns, as shown in FIGS. 7 and 8, respectively.

Figure 7:
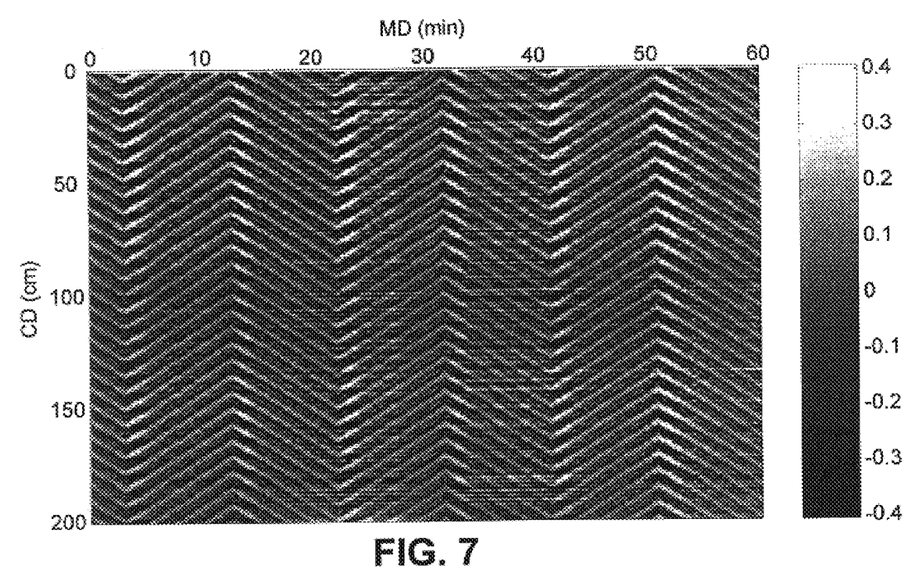
FIGS. 7 and 8 are images of detailed diagnostic patterns separated from the diagnostic variation pattern of FIG. 5.
Figure 9:
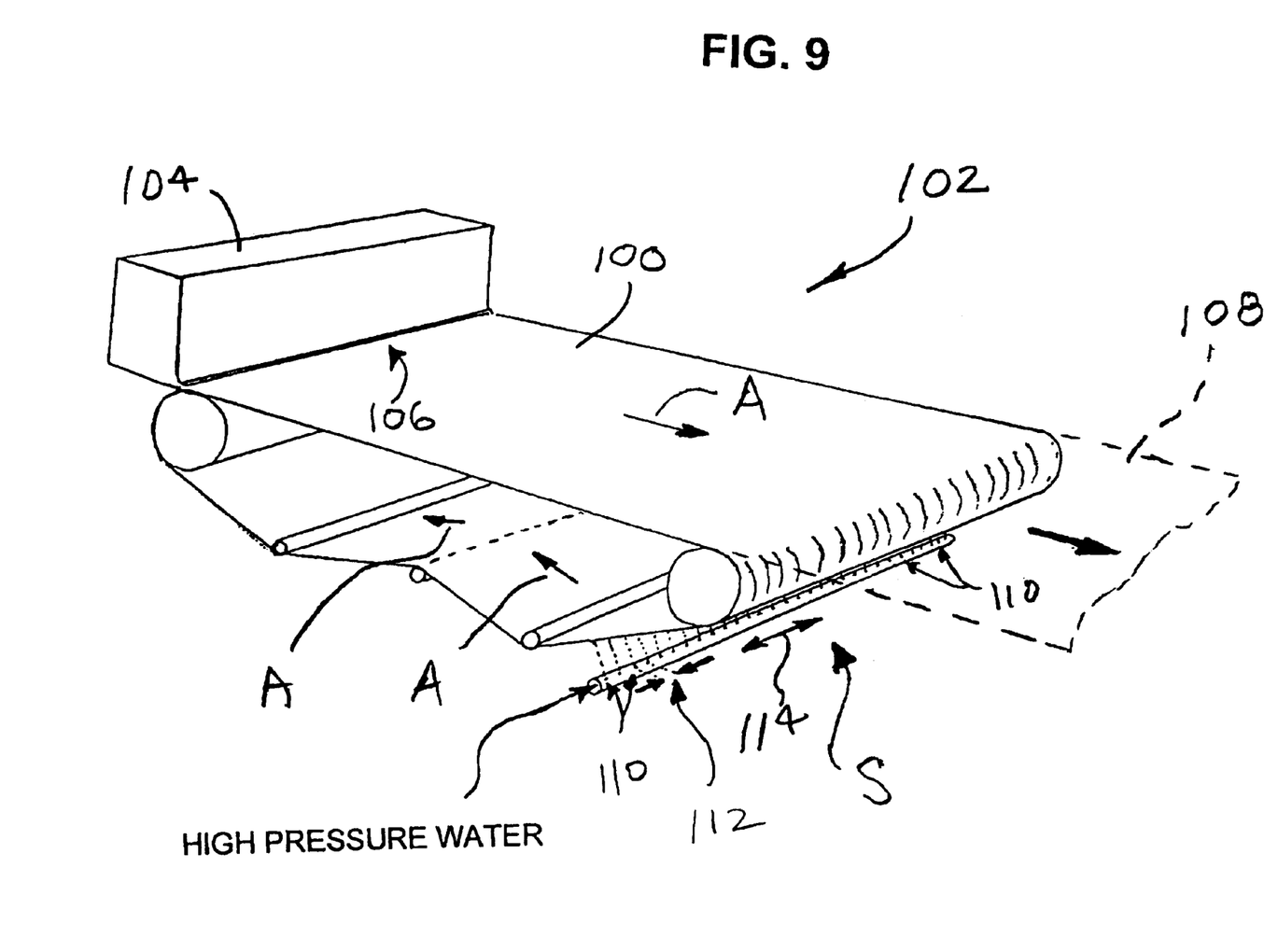
FIG. 9 is a schematic illustration of a high-pressure water shower that is applied to clean a Fourdriner wire of a paper making machine.

In this example, the first diagnostic pattern, pattern 1 of FIG. 7, is linked to a high-pressure water shower S that is applied to clean a Fourdrinier wire 100 of a paper-making machine 102 as shown schematically in FIG. 9. The paper-making machine 102 includes a headbox 104 which deposits pulp slurry through a slice lip 106 onto the Fourdrinier wire 100 to form a sheet of paper 108. The Fourdrinier wire 100 is moving in the direction of the arrows A with the sheet of paper 108 traveling along the upper portion of the wire and being separated from the wire as shown. The shower S has a large array of nozzles 110 that are spaced about 7.5 cm apart as shown at 112. The shower S and, hence, the entire array of water nozzles 110 "strokes" or moves back and forth approximately 30 cm in the cross-machine direction as shown by the arrow 114. The stroking period is approximately 20 minutes per cycle as can be discerned from FIG. 7.

Figure 8:
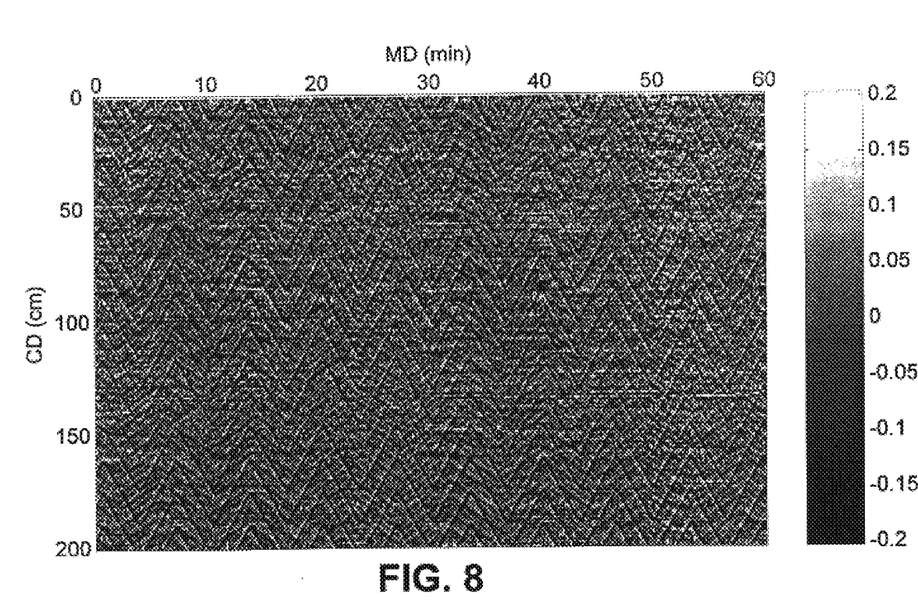

The second diagnostic pattern, pattern 2 of FIG. 8, is linked to a similar second high-pressure water shower (not shown) that is applied under a felt in a press section of the paper-making machine 102 where the press section is not shown but is common in paper-making machines. The spacing of an array of nozzles for this shower is approximately 15 cm and the shower has a stroking period of about 7.5 minutes per cycle as can be discerned from FIG. 8.

The above example illustrates how decomposition of two-dimensional measurement data into two-dimensional (2D) variation patterns and classification of the variation patterns in accordance with the present invention can be applied to extract useful information for control and diagnosis purposes. This new way of extracting or separating sheet variations and classifying those sheet variations is very useful to help users visualize any problem of sheet variations and can be used to create new control schemes to improve sheet quality.

The technique used to extract multiple variation patterns from a 2D measurement is derived from the concept of functional decomposition. For a given 2D sheet variation $y(x,t)$ where x represents a CD location and t represents time in the machine direction, $y(x,t)$ can be treated as the combination of a group of basis functions $\phi_k(x,t)$ as:

$$y(x,t) = \sum_k c_k \varphi_k(x,t) \tag{9}$$

After selecting a proper set of basis functions, each coefficient $c_k$ can be derived by convoluting each basis function $\phi_k(x,t)$ with $y(x,t)$. In practice, $y(x,t)$ is usually sampled or discretized into a 2D array or matrix Y as represented in equation (1). For a discretized 2D array Y, only a finite number of basis functions and their corresponding coefficients $c_k$ are needed to decompose Y as:

$$Y = \sum_{k=1}^{N} c_k \varphi_k \tag{10}$$

where $\phi_k$ is the discretized one or two dimensional array (i.e. basis vector or basis matrix) which is equivalent to the basis function $\phi_k(x,t)$ in the continuous expression.

The basis functions $\phi_k(x,t)$ are either pre-defined or derived from the sheet variation measurements depending on the type of variations to be extracted. For example, to extract the pure machine direction variation, the basis function is defined as:

$$\varphi_j^{md}(x,t) = \delta(t-t_j) \quad \text{for } 0 \leq x \leq W \tag{11}$$
$$= 0 \quad \text{for all other } x$$

where W is the width of the sheet and for $t_a \leq t \leq t_b$ $$\delta(t-t_j) = 1 \quad \text{if } t = t_j \tag{12}$$
$$= 0 \quad \text{if } t \neq t_j$$

where $t_a$ and $t_b$ are the beginning and the ending points of the MD time interval of the selected 2D sheet variation.

The coefficient $c_j^{md}$ corresponding to the above MD basis function $\phi_j^{md}(x,t)$ is calculated as:

$$c_j^{md} = \tag{13}$$
$$\int_0^W \int_{t_a}^{t_b} \varphi_j^{md}(x,t) y(x,t) \, dt \, dx \Big/ \int_0^W \int_{t_a}^{t_b} \varphi_j^{md}(x,t) \varphi_j^{md}(x,t) \, dt \, dx$$

In the discrete form, the basis vector $\phi^{md}$ to extract the MD variation is:

$$\varphi^{md} = \varphi_j^{md} = \begin{bmatrix} 1 \\ 1 \\ 1 \\ \vdots \\ 1 \end{bmatrix}_{n \times 1} \tag{14}$$

and its corresponding coefficient $c_j^{md}$ is:

$$c_j^{md} = ((\varphi_j^{md})^T \varphi_j^{md})^{-1} (\varphi_j^{md})^T y_j = \frac{1}{n} \sum_{i=1}^{n} y(i,j) \tag{15}$$

where $y_j$ is the j-th column of Y.

The whole range of the MD variations within the time interval is expressed by the vector:

$$c^{md} = ((\phi^{md})^T \phi^{md})^{-1} (\phi^{md})^T Y \tag{16}$$

where $c^{md}$ is a row vector having a size of 1×m.

The MD variation $Y_{md}$ expressed as a 2D matrix is:

$$Y_{md} = \phi^{md} c^{md} \tag{17}$$

The sheet variation without the MD component is derived as:

$$Y_0 = Y - Y_{md} = [y(i,j) - c_j^{md}] = [y_0(i,j)] \tag{18}$$

The controllable CD variations $Y_{cc}$ are closely correlated with the CD response of each CD actuator. To extract the CD variations that are controllable with the k-th CD atuator, the basis function is set to:

$$\phi_k^{cc}(x,t) = g_k(x) \tag{19}$$

where $g_k(x)$ is the response of the k-th CD actuator.

In the discrete form, the basis vector to extract CD variations that are controllable with the k-th CD actuator is:

$$\phi_k^{cc} = g_k \tag{20}$$

To extract all controllable CD variations, the basis matrix is set to the CD controllable basis matrix $\phi^{cc}$:

$$\phi^{cc} = G = [g_k]_{n \times n_a} \tag{21}$$

where G is the full CD response matrix and $n_a$ is the number of CD actuators.

The CD actuator response G can be identified using known techniques, for example, the method described in U.S. Pat. No. 5,122,963, which is incorporated herein by reference, may be used to identify the CD actuator response G.

The decomposition coefficients $C^{cc}$ corresponding to the CD controllable basis matrix $\phi^{cc}$ are calculated as:

$$C^{cc} = (G^T G)^{-1} G^T Y_0 \tag{22}$$

and the CD controllable variation is:

$$Y_{cc} = \phi^{cc} C^{cc} = G C^{cc} \tag{23}$$

In case that $G^T G$ is singular or near singular (i.e. the inverse of $G^T G$ is not feasible), $G^T G$ can be decomposed using singular value decomposition as:

$$G^T G = V S V^T \tag{24}$$

where each column of the matrix V is an eigenvector of the matrix $G^TG$. S is a diagonal matrix with its diagonal elements being the singular values of $G^TG$. The singular values are sorted in a descending order in forming S and V. By keeping the significant singular values and their corresponding eigenvectors, the matrix $G^TG$ can be approximated as:

$$G^TG \cong \hat{V}\hat{S}\hat{V}^T \qquad (25)$$

where $\hat{S}$ and $\hat{V}$ are constructed with the significant singular values and their corresponding eigenvectors, respectively.

The inverse of $G^TG$ is approximated with:

$$(G^TG)^{-1} \cong [(\hat{V}^T\hat{V})^{-1}\hat{V}^T]^T\hat{S}^{-1}(\hat{V}^T\hat{V})^{-1}\hat{V}^T \qquad (26)$$

After the MD variations $Y_{md}$ and controllable CD variation $Y_{cc}$ are removed from the 2D sheet variation Y, the remaining sheet variation $Y_r$ (also called 2D residual variation) is calculated as:

$$Y_r = Y - Y_{md} - Y_{cc} \qquad (27)$$

The residual variation $Y_r$ contains the variations that are likely related to some process problems. If pre-knowledge of the sheet variation to be diagnosed is available, the basis functions for the diagnosis patterns can be pre-defined according to the characteristics of the known sheet variation patterns. Otherwise, well-known functions such as sinusoidal functions, orthogonal polynomials, wavelet scale and detail functions, or the principal components of $Y_r$ can be used.

One useful set of basis functions or matrices can be derived from the singular value decomposition of the covariance matrix of the 2D variation $Y_r$. The covariance matrix of a 2D variation matrix $Y_r$ is $Y_rY_r^T$ or $Y_r^TY_r$. The singular value decomposition of $Y_rY_r^T$ is:

$$Y_rY_r^T = UDU^T \qquad (28)$$

where each column of the U matrix is an eigenvector of the covariance matrix $Y_rY_r^T$ and D is a diagonal matrix with diagonal elements being the singular values of $Y_rY_r^T$ corresponding to those eigenvectors in U. The eigenvectors and singular values are sorted in descending order in forming U and D. Each eigenvector in U represents one CD basis function or vector. By using these basis vectors to decompose $Y_r$, a group of MD basis vectors can be obtained as:

$$A^T = (U^TU)^{-1}U^TY_r \qquad (29)$$

where each row of $A^T$ represents a MD basis vector.
The 2D variation $Y_r$ can be decomposed as:

$$Y_r = UA^T = \sum_{k=1}^{\min(m,n)} u_k a_k^T \qquad (30)$$

where $u_k$ is the k-th column of U and $a_k^T$ is the k-th row of $A^T$. If each row of $A^T$ is normalized with its norm to get the normalized row vector $v_k^T$ as:

$$v_k^T = a_k^T/c_k \text{ with } c_k = \|a_k^T\| \qquad (31)$$

then $$Y_r = \sum_{k=1}^{\min(m,n)} c_k u_k v_k^T = \sum_{k=1}^{\min(m,n)} c_k \varphi_k^d \qquad (32)$$

where $\varphi_k^d = u_k v_k^T$ represents the k-th 2D basis matrix.

Figure 10:
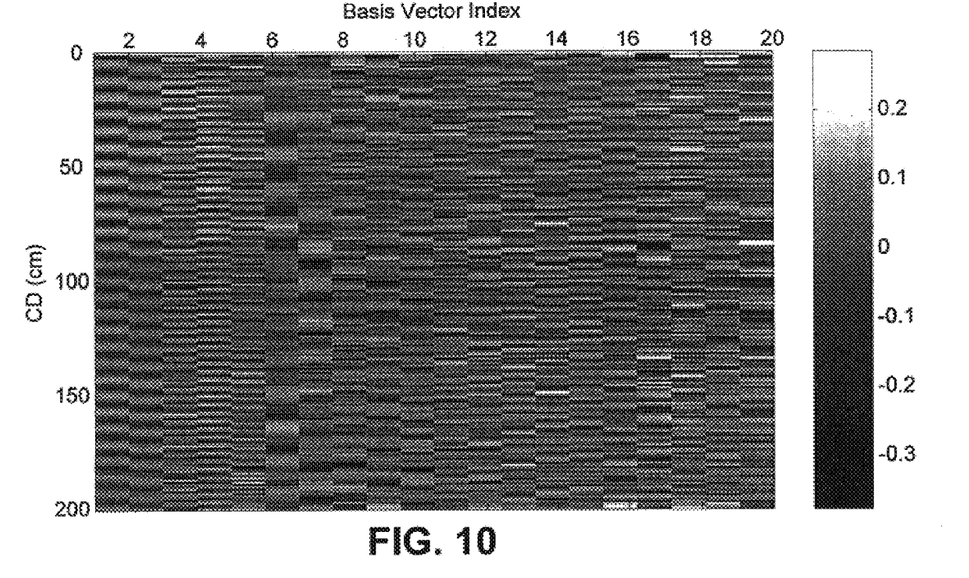
FIGS. 10 and 11 illustrate the first 20 CD and MD basis vectors, respectively, obtained from the 2D residual variations of sheet measurement of FIG. 1 using single value decomposition techniques. The CD basis vectors are columns of FIG. 10 and the MD basis vectors are rows of FIG. 11.
Figure 11:
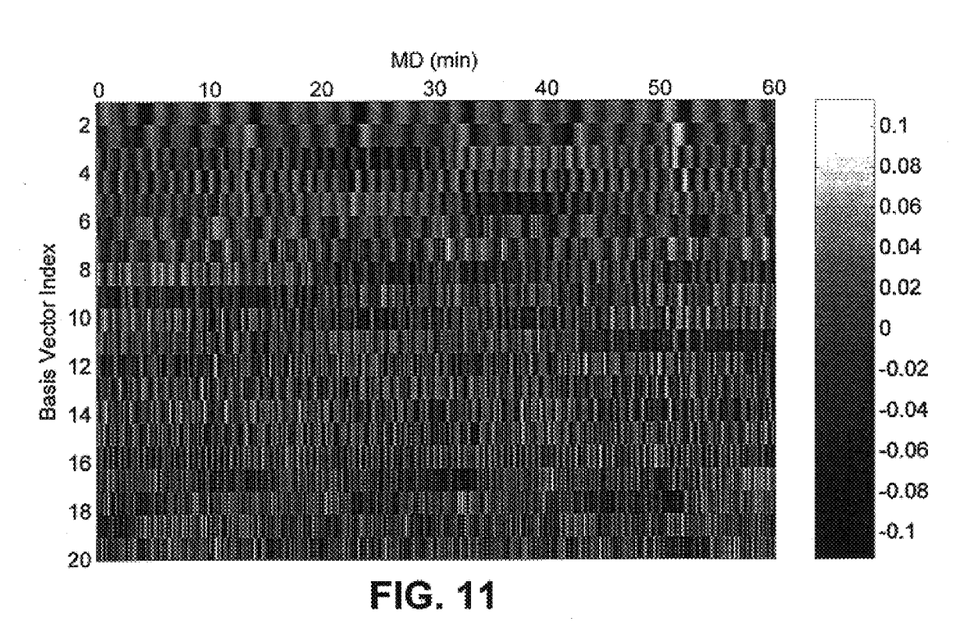
Figure 12:
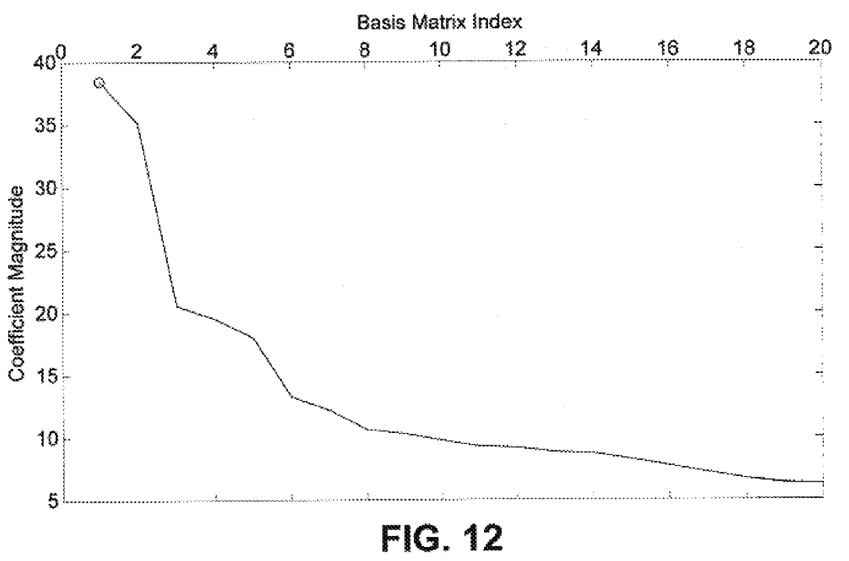
FIG. 12 plots the first 20 coefficients corresponding to the first 20 2D basis matrices that are used to decompose the 2D residual variations of the sheet measurement of FIG. 1.
Figure 13:
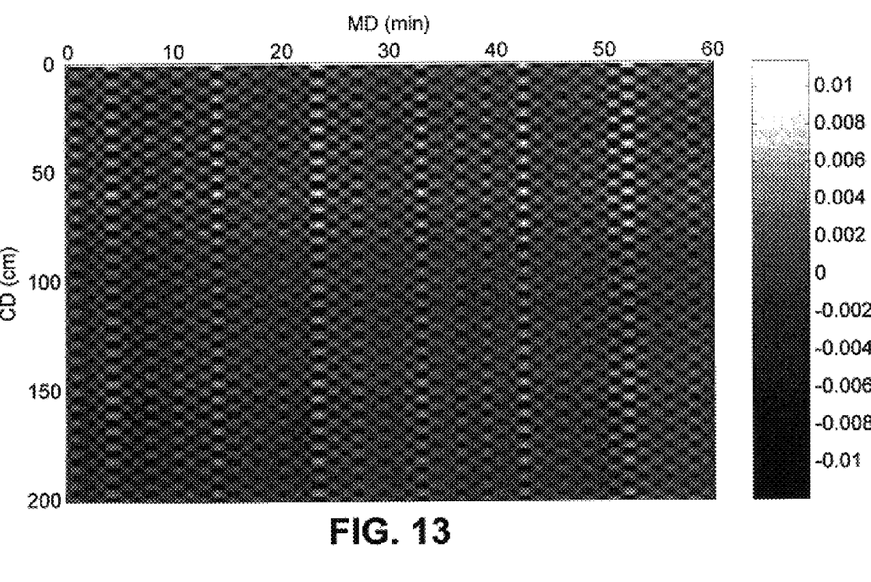
FIG. 13 is an image of the first 2D basis matrix that is formed from the first CD basis vector (column) of FIG. 10 and the first MD basis vector (row) of FIG. 11.

FIGS. 10 and 11 display the first 20 CD and MD basis vectors that are derived from the residual variations $Y_r$ of the 2D measurement of FIG. 1. The decomposition coefficients $c_k$ of the example measurement of FIG. 1 are shown in FIG. 12. An image of the first 2D basis matrix that is the product of the first pair of CD and MD basis vectors shown in FIGS. 10 and 11 is displayed in FIG. 13.

Figure 14:
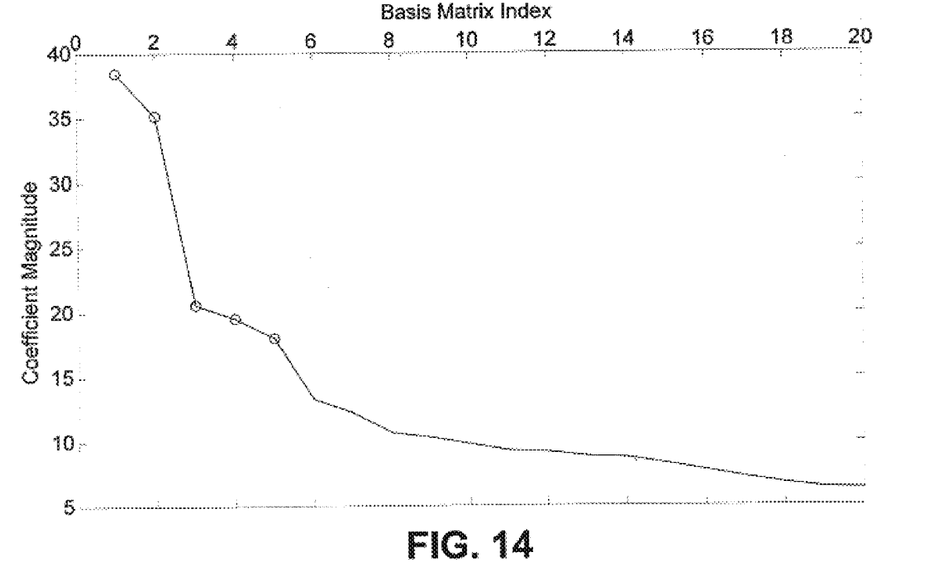
FIG. 14 indicates the first 5 coefficients that are used to construct the first diagnostic variation pattern shown in FIG. 15.
Figure 15:
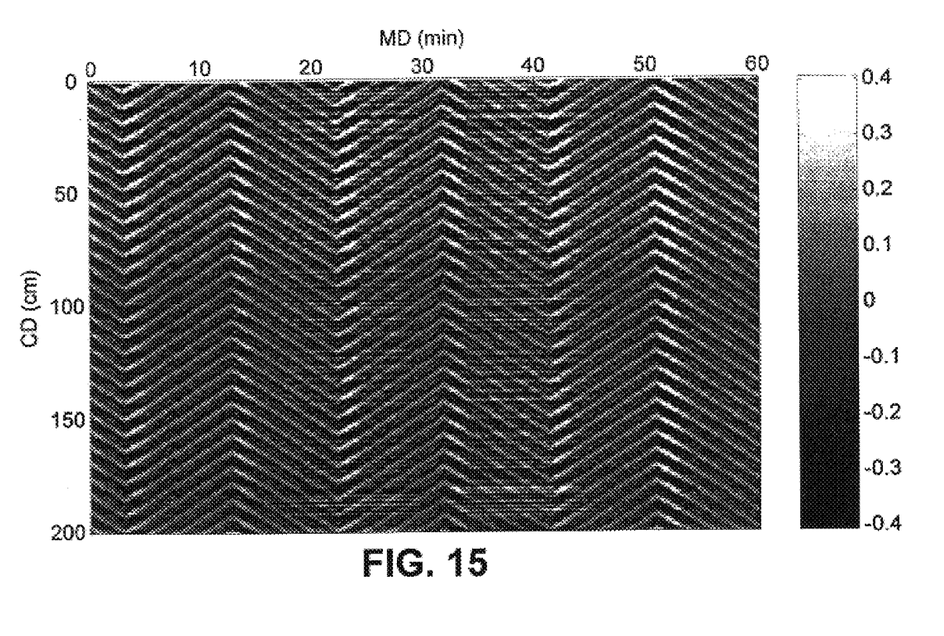
FIG. 15 is the image of the first diagnostic variation pattern constructed from the first 5 pairs of basis vectors of FIGS. 10 and 11 and the corresponding coefficients of FIG. 14.
Figure 16:
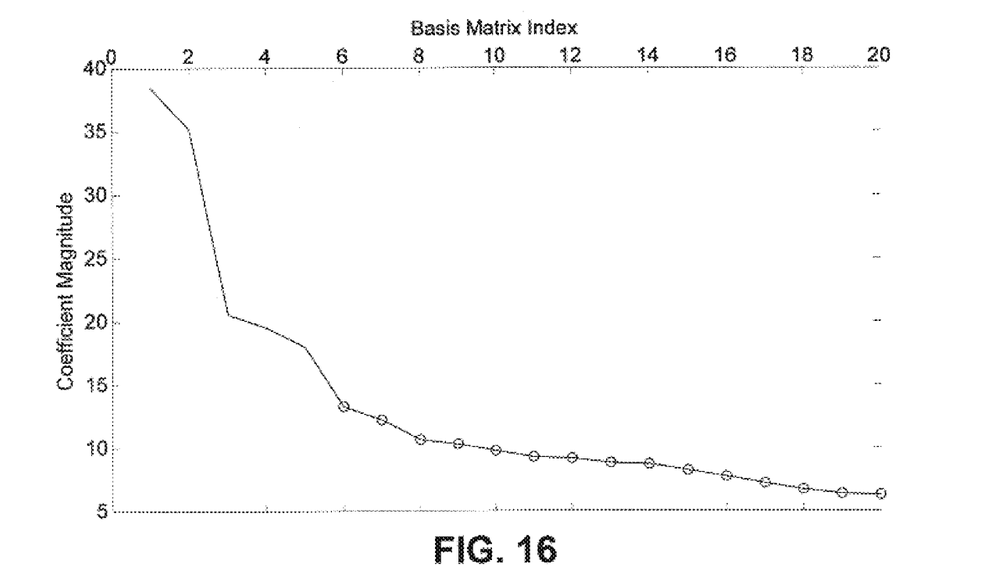
FIG. 16 indicates the 6-th through 20-th coefficients that are used to construct the second diagnostic variation pattern shown in FIG. 17.
Figure 17:
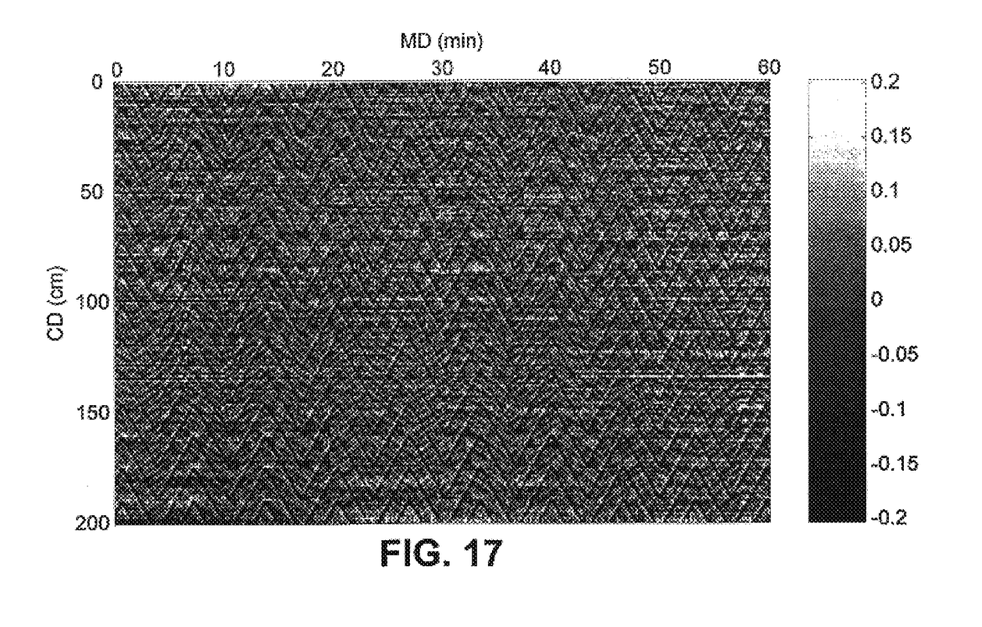
FIG. 17 is the image of the second diagnostic variation pattern constructed from the 6-th to 20-th pairs of basis vectors of FIGS. 10 and 11 and the corresponding coefficients of FIG. 16.

For the illustrative example, the first diagnostic variation pattern as shown in FIG. 15 is constructed from the first 5 weighting coefficients of FIG. 14 and the first 5 pairs of CD and MD basis vectors in FIGS. 10 and 11, respectively. Similarly, the second diagnostic variation pattern as shown in FIG. 17 is constructed from the 6-th through 20-th weighting coefficients of FIG. 16 and the 6-th through 20-th pairs of CD and MD basis vectors in FIGS. 10 and 11, respectively.

The basis matrix $\varphi_k^d$ essentially captures the key features of each class of sheet variation. If the variations in $Y_r$ are totally random, then $c_k$ appears to be decreasing uniformly. If the variations in $Y_r$ show any detectable pattern, $c_k$ becomes a concave curve, i.e. $c_k$ decays rapidly for several initial coefficients and decreases slowly for the rest of the coefficients. Usually a few distinct break points can be found. The variation pattern changes distinctively at the break points of $c_k$. The different variation patterns can also be distinguished by examining the spectral contents of each individual basis vector $u_k$ or $v_k^T$. A user can use the break points in $c_k$ or the spectral characteristics of each basis vector to separate 2D basis matrices into several groups $I_1, I_2, I_3, \ldots, I_s$. Each group is a subset of $\{1, 2, 3, \ldots, \min(n,m)\}$. By combining each group of basis matrices, a particular variation pattern is extracted.

$$Y_{dl} = \sum_{k \in I_l} c_k \varphi_k^d \text{ where } I_l \text{ is a subset of } \{1, 2, 3, \ldots, \min(n, m)\} \qquad (33)$$

Finally, the part of the variations that are almost completely random and have no significant pattern is considered as the unclassifiable variation pattern $Y_u$. $Y_u$ is whatever is left of $Y_r$ after all recognizable patterns are completely separated or removed.

In summary, for a given 2D sheet variation Y, the pattern extraction and classification technique can be described as:

$$Y = Y_{md} + Y_{cc} + Y_d + Y_u \qquad (34)$$

$$= \varphi^{md}c^{md} + \varphi^{cc}C^{cc} + \sum_{k \in I_1} c_k \varphi_k^d + \sum_{k \in I_2} c_k \varphi_k^d + \ldots + Y_u$$

where the first term on the right-hand side of the above equation is the MD variation pattern, the second term is the CD controllable variation pattern, the third term is the first diagnosis pattern, the fourth term is the second diagnosis pattern, and the last term is the remaining unclassifiable variations. The actual procedure of separating and classifying these patterns is executed in the following steps:

1. Select the proper CD and MD ranges of sheet variations Y to be analyzed.
2. Remove spikes (abnormal measurements) as needed.

3. Separate or remove the MD variations $Y_{md}$ so that the remaining variation is $Y_0$.
4. Separate CD controllable variations $Y_{cc}$ from $Y_0$. The remaining variation is $Y_r$.
5. Perform singular value decomposition of $Y_r Y_r^T$ and find MD basis vectors corresponding to their CD basis vectors which are the eigenvectors of $Y_r Y_r^T$.
6. Form diagnosis basis matrices $\phi_k^d$ from MD and CD basis vectors determined from step 5.
7. Separate diagnosis basis matrices $\phi_k^d$ into several subgroups and reconstruct distinguishable variation patterns.
8. The random components are combined together to form the unclassifiable variations.
9. Perform spectral analysis and calculate variability of each separated variation pattern.
10. Display each variation pattern and plot its variability and spectral contents.

Important aspects of the new variation analysis technique of the present invention are:

1. A new way of expressing a 2D sheet variation is derived for a truly two-dimensional measurement from either scanning or non-scanning sensors. Given a two-dimensional measurement, the sheet variations are decomposed into several main classes: MD variations, controllable CD variations, diagnostic variations, and unclassifiable variations. Each class of variations can be further decomposed into even more detailed patterns. This way of analyzing a 2D measurement extracts more useful information contained in a 2D measurement of sheet variations.
2. Each classified pattern is strongly linked to either a controllable actuator or a portion of the process equipment or machine such as the high-pressure water showers under the Fourdriner wires or felts. The connection between each pattern and its root cause provides the user of the process or machine with an opportunity to improve control performance or to project the potential improvement with a proper adjustment applied to the process or machine. The separated patterns are more direct indications of control results and the performance of machine settings.
3. The new pattern extraction technique of the present invention opens new windows of process visibility. The extracted variation patterns can lead to new ways to improve sheet variations. For example, since the impacts of the high-pressure water shower can be seen in the extracted pattern, these water showers can be utilized as process actuators to control the corresponding sheet variation pattern. Thus, more uniform sheet material can be achieved by changing the drainage of Fourdrinier wires or by changing the method of felt cleaning.
4. The new pattern extraction technique of the present invention can also be used to extract process response models effectively. One example is to identify response models of process actuators. A group of pre-defined patterns can be generated and applied to a group of process actuators as perturbing actions. These pre-defined patterns are later used as the basis functions to decompose the resulting 2D measurement. The sheet variations that are well correlated to those pre-defined patterns will be the response models of the process actuators.
5. Another potential application of the decomposition technique of the present invention is for separating measurements derived from a composite material. For example, a 2D measurement may be the superposition of the variations of a sheet of material and a substrate which supports the sheet, for example a paper sheet supported upon a felt or a Fourdrinier wire. If the substrate has distinguishable pattern characteristics, then the described decomposition method of the present application can be used to separate the substrate variations from the sheet variations. The decomposition technique of the present invention can therefore enhance a user's ability to detect sheet variations at various locations along the path of production even though the sheet is not totally free from supporting structure such as felts or a forming wire of a paper making machine.

Having thus described the invention of the present application in detail and by reference to preferred embodiments thereof, it will be apparent that modifications and variations are possible without departing from the scope of the invention defined in the appended claims.

What is claimed is:

1. A method for determining variations of a sheet of material as said sheet of material is being manufactured comprising the steps of:

measuring at least one characteristic of said sheet across at least a portion of an entire width of said sheet to generate a two-dimensional measurement of sheet variations;

identifying at least one variation pattern which can be within said two-dimensional measurement as a result of manufacture of said sheet by determining at least one basis function closely associated with said variation pattern;

processing said two-dimensional measurement to extract a variation pattern corresponding to said at least one variation pattern from said two-dimensional measurement by:

convoluting said at least one basis function with said two-dimensional measurement to get a coefficient corresponding to said basis function; and constructing said variation pattern as a combination of said coefficient with said basis function; and utilizing said extracted variation pattern for the manufacture of said sheet of material.

2. A method for determining variations of a sheet of material as said sheet of material is being manufactured as claimed in claim 1 wherein said at least one variation pattern corresponds to quality variations of said sheet of material and said step of utilizing said extracted variation pattern for the manufacture of said sheet of material comprises the step of utilizing said extracted variation pattern as a representation of the quality of said sheet of material.

3. A method for determining variations of a sheet of material as said sheet of material is being manufactured as claimed in claim 1 further comprising the step of associating said at least one pattern with operation of said system and wherein said step of utilizing said extracted variation pattern for the manufacture of said sheet of material comprises the step of utilizing said at least one pattern to analyze operation of said system.

4. A method for determining variations of a sheet of material as said sheet of material is being manufactured as claimed in claim 1 further comprising the step of associating said at least one pattern with operation of said system and wherein said step of utilizing said extracted variation pattern for manufacture of said sheet of material comprises the step of controlling said system to affect said at least one pattern.

5. A method for determining variations of a sheet of material as said sheet of material is being manufactured as claimed in claim 4 wherein said step of controlling said operation of said system to affect said at least one pattern comprises the step of changing said operation of said system so that said at least one pattern is minimized.

6. A method for determining variations of a sheet of material as said sheet of material is being manufactured as claimed in claim 1 further comprising the step of associating said at least one pattern with operation of said system and wherein said step of utilizing said extracted variation pattern for manufacture of said sheet of material comprises the step of monitoring operation of said system.

7. A method for determining variations of a sheet of material as said sheet of material is being manufactured as claimed in claim 1 wherein said step of identifying at least one variation pattern which can be within said two-dimensional measurement as a result of manufacture of said sheet comprises the step of determining a set of basis functions closely associated with said variation pattern.

8. A method for determining variations of a sheet of material as said sheet of material is being manufactured as claimed in claim 7 wherein said step of processing said two-dimensional measurement to extract a variation pattern corresponding to said at least one variation pattern from said two-dimensional measurement comprises the steps of:
    convoluting said set of basis functions with said two-dimensional measurement to get a set of coefficients corresponding to said set of basis functions; and
    constructing said variation pattern as a linear combination of said set of coefficients with said set of basis functions.

9. A method for determining variations of a sheet of material as said sheet of material is being manufactured as claimed in claim 1 wherein said step of measuring at least one characteristic of said sheet across at least a portion of an entire width of said sheet comprises the step of measuring at least one characteristic of said sheet substantially across said entire width of said sheet of material.

10. A method for determining variations of a sheet of material as said sheet of material is being manufactured comprising the steps of:
    measuring at least one characteristic of said sheet across at least a portion of an entire width of said sheet to generate a two-dimensional measurement of sheet variations;
    identifying at least one variation pattern which can be within said two-dimensional measurement as a result of manufacture of said sheet by determining at least one basis vector closely associated with said variation pattern;
    processing said two-dimensional measurement to extract a variation pattern corresponding to said at least one variation pattern from said two-dimensional measurement; and
    utilizing said extracted variation pattern for the manufacture of said sheet of material.

11. A method for determining variations of a sheet of material as said sheet of material is being manufactured comprising the steps of:
    measuring at least one characteristic of said sheet across at least a portion of an entire width of said sheet to generate a two-dimensional measurement of sheet variations;
    identifying at least one variation pattern which can be within said two-dimensional measurement as a result of manufacture of said sheet by determining a set of basis vectors closely associated with said variation pattern;
    processing said two-dimensional measurement to extract a variation pattern corresponding to said at least one variation pattern from said two-dimensional measurement; and
    utilizing said extracted variation pattern for the manufacture of said sheet of material.

12. A method for determining variations of a sheet of material as said sheet of material is being manufactured as claimed in claim 11 wherein said step of processing said two-dimensional measurement to extract a variation pattern corresponding to said at least one variation pattern from said two-dimensional measurement comprises the steps of:
    convoluting said set of basis vectors with said two-dimensional measurement to get a set of coefficients corresponding to said set of basis vectors; and
    constructing said variation pattern as a linear combination of said set of coefficients with said set of basis vectors.

13. A method for determining variations of a sheet of material as said sheet of material is being manufactured comprising the steps of:
    measuring at least one characteristic of said sheet across at least a portion of an entire width of said sheet to generate a two-dimensional measurement of sheet variations;
    identifying at least one variation pattern which can be within said two-dimensional measurement as a result of manufacture of said sheet by determining at least one basis matrix closely associated with said variation pattern;
    processing said two-dimensional measurement to extract a variation pattern corresponding to said at least one variation pattern from said two-dimensional measurement; and
    utilizing said extracted variation pattern for the manufacture of said sheet of material.

14. A method for determining variations of a sheet of material as said sheet of material is being manufactured comprising the steps of:
    measuring at least one characteristic of said sheet across at least a portion of an entire width of said sheet to generate a two-dimensional measurement of sheet variations;
    identifying at least one variation pattern which can be within said two-dimensional measurement as a result of manufacture of said sheet by determining a set of basis matrices closely associated with said variation pattern;
    processing said two-dimensional measurement to extract a variation pattern corresponding to said at least one variation pattern from said two-dimensional measurement; and
    utilizing said extracted variation pattern for the manufacture of said sheet of material.

15. A method for determining variations of a sheet of material as said sheet of material is being manufactured as claimed in claim 14 wherein said step of processing said two-dimensional measurement to extract a variation pattern corresponding to said at least one variation pattern from said two-dimensional measurement comprises the steps of:
    convoluting said set of basis matrices with said two-dimensional measurement to get a set of coefficients corresponding to said set of basis matrices; and
    constructing said variation pattern as a linear combination of said set of coefficients with said set of basis matrices.

16. A method for determining variations of a sheet of material as said sheet of material is being manufactured comprising the steps of:
- measuring at least one characteristic of said sheet across at least a portion of an entire width of said sheet to generate a two-dimensional measurement;
- identifying a plurality of variation patterns which can be within said two-dimensional measurement as a result of manufacture of said sheet;
- processing said two-dimensional measurement to extract at least one of said plurality of variation patterns contained within said two-dimensional measurement; and
- utilizing said at least one extracted variation pattern for manufacture of said sheet of material.

17. A method for determining variations of a sheet of material as said sheet of material is being manufactured as claimed in claim 16 wherein said step of processing said two-dimensional measurement to extract at least one of said plurality of variation patterns comprises the step or processing said two-dimensional measurement to extract two or more of said plurality of variation patterns, and said step of utilizing said at least one extracted variation pattern comprises the step of utilizing said two or more extracted variation patterns.

18. A method for characterizing separate components of a composite material sheet, made up of at least two layers, said method comprising the steps of:
- measuring at least one characteristic of said composite material sheet across at least a portion of an entire width of said sheet to generate a two-dimensional measurement;
- classifying component patterns contained within said two-dimensional measurement and corresponding to said at least two layers;
- processing said two-dimensional measurement to extract at least one component pattern contained within said two-dimensional measurement; and
- separating said at least one component pattern from said two-dimensional measurement to enable evaluation of a remainder of said composite material sheet.

19. A method for characterizing separate layers of a composite material sheet, made up of at least two layers, as claimed in claim 18 wherein said composite material sheet comprises a first layer of material being manufactured and a second layer supporting said first layer of material, said step of processing said two-dimensional measurement to extract at least one component pattern contained within said two-dimensional measurement comprises the step of processing said two-dimensional measurement to extract a component pattern corresponding to said second layer of material and said step of separating said at least one component pattern from said two-dimensional measurement comprises the step of separating said component pattern corresponding to said second layer from said two-dimensional measurement to derive an effective measurement corresponding to said first layer of material being manufactured.

20. A method for characterizing separate layers of a composite material sheet, made up of at least two layers, as claimed in claim 19 further comprising the step of evaluating said effective measurement to evaluate said first layer of material being manufactured.

21. A method for extracting process response models from a measurement of a sheet of material as said sheet of material is being manufactured, said method comprising the steps of:
- applying a group of pre-defined patterns to a group of process actuators used to manufacture said sheet of material;
- measuring at least one characteristic of said sheet of material across at least a portion of an entire width of said sheet to generate a two-dimensional measurement;
- processing said two-dimensional measurement to identify variation patterns that are associated with said group of pre-defined patterns; and
- convoluting said group of pre-defined patterns with said measurement to extract process response models that correspond to said group of process actuators.

* * * * *

UNITED STATES PATENT AND TRADEMARK OFFICE
CERTIFICATE OF CORRECTION

PATENT NO. : 6,411,860 B1
DATED : June 25, 2002
INVENTOR(S) : Shih-Chin Chen

It is certified that error appears in the above-identified patent and that said Letters Patent is hereby corrected as shown below:

Column 6,
Line 32, "k-th CD atuator" should read -- k-th CD actuator --;

Column 7,
Equation 25, "$G^T G \equiv \hat{V} \hat{S} \hat{V}^T$" should read -- $G^T G \cong \hat{V} \hat{S} \hat{V}^T$ --;

Equation 26, "$(G^T G)^{-1} \equiv [(\hat{V}^T \hat{V})^{-1} \hat{V}^T]^T \hat{S}^{-1} (\hat{V}^T \hat{V})^{-1} \hat{V}^T$" should read -- $(G^T G)^{-1} \cong [(\hat{V}^T \hat{V})^{-1} \hat{V}^T]^T \hat{S}^{-1} (\hat{V}^T \hat{V})^{-1} \hat{V}^T$ --;

Column 13,
Line 21, "step or processing" should read -- step of processing --.

Signed and Sealed this

Thirtieth Day of March, 2004

JON W. DUDAS
*Acting Director of the United States Patent and Trademark Office*